(12) United States Patent
Maierhofer et al.

(10) Patent No.: US 10,896,755 B2
(45) Date of Patent: Jan. 19, 2021

(54) REMOTE CONTROL OF MESSAGES FOR A DIALYSIS APPARATUS

(71) Applicant: Fresenius Medical Care Deutschland GmbH, Bad Homburg (DE)

(72) Inventors: Andreas Maierhofer, Schweinfurt (DE); Carsten Müller, Euerbach (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 1008 days.

(21) Appl. No.: 15/429,827

(22) Filed: Feb. 10, 2017

(65) Prior Publication Data

US 2017/0270264 A1 Sep. 21, 2017

(30) Foreign Application Priority Data

Mar. 21, 2016 (DE) .................. 10 2016 105 199

(51) Int. Cl.
| | | |
|---|---|---|
| *G16H 40/67* | (2018.01) | |
| *G16H 40/63* | (2018.01) | |
| *A61M 1/14* | (2006.01) | |
| *G16H 20/40* | (2018.01) | |

(52) U.S. Cl.
CPC .............. *G16H 40/67* (2018.01); *A61M 1/14* (2013.01); *G16H 40/63* (2018.01); *A61M 2205/18* (2013.01); *A61M 2205/3553* (2013.01); *A61M 2205/505* (2013.01); *A61M 2205/609* (2013.01); *A61M 2205/6063* (2013.01); *G16H 20/40* (2018.01)

(58) Field of Classification Search
CPC ........ G16H 40/67; G16H 40/63; G16H 20/40; A61M 1/14; A61M 2205/18; A61M 2205/3553; A61M 2205/505; A61M 2205/6063; A61M 2205/609
USPC ........................................................ 705/2–3
See application file for complete search history.

(56) References Cited

U.S. PATENT DOCUMENTS

| 9,189,597 B2 | 11/2015 | Bluemler et al. | |
| 2003/0227386 A1* | 12/2003 | Pulkkinen | G16H 40/20 340/573.1 |

(Continued)

FOREIGN PATENT DOCUMENTS

| DE | 197 42 633 A1 | 4/1999 |
| DE | 10 2007 002305 A1 | 7/2008 |

(Continued)

OTHER PUBLICATIONS

Thimbleby, Improving Safety in Medical Devices and Systems, Sep. 1, 2013, 2013 IEEE International Conference on Healthcare Informatics, pp. 1-13 (Year: 2013).*

(Continued)

*Primary Examiner* — Joy Chng
(74) *Attorney, Agent, or Firm* — Leydig, Voit & Mayer, Ltd.

(57) ABSTRACT

Alarm messages, which are output by a medical apparatus, are remotely processed on a remote application apparatus under consideration of a safety check and in particular with regard to whether the user who is working at the application apparatus is in visual contact with the alarm message-triggering medical apparatus. The medical apparatus may be a hemodialysis apparatus or a peritoneal dialysis apparatus, or another type of medical apparatus.

23 Claims, 2 Drawing Sheets

(56) References Cited

U.S. PATENT DOCUMENTS

| | | | |
|---|---|---|---|
| 2006/0154642 A1* | 7/2006 | Scannell, Jr. | G08B 7/066 455/404.1 |
| 2008/0004502 A1* | 1/2008 | Ash | G16H 80/00 600/300 |
| 2010/0318578 A1* | 12/2010 | Treu | G16H 40/67 707/802 |
| 2011/0107251 A1* | 5/2011 | Guaitoli | G06F 19/3418 715/772 |
| 2012/0138533 A1* | 6/2012 | Curtis | A61M 1/16 210/646 |
| 2013/0018355 A1 | 1/2013 | Brand et al. | |
| 2013/0131845 A1 | 5/2013 | Guilleminot | |
| 2013/0133036 A1 | 5/2013 | Wang et al. | |
| 2014/0113553 A1 | 4/2014 | Brukalo et al. | |
| 2014/0266983 A1* | 9/2014 | Christensen | A61M 1/3607 345/8 |

FOREIGN PATENT DOCUMENTS

| | | |
|---|---|---|
| DE | 10 2011 107795 A1 | 1/2013 |
| EP | 1 480 180 A1 | 11/2004 |

OTHER PUBLICATIONS

International Patent Application PCT/EP2017/056535, International Search Report (dated Jun. 22, 2017).

\* cited by examiner

REMOTE CONTROL OF MESSAGES FOR A DIALYSIS APPARATUS

CROSS-REFERENCE TO RELATED APPLICATIONS

Priority is claimed to German Patent Application No. DE 102016105199.3, filed on Mar. 21, 2016, the entire disclosure of which is hereby incorporated by reference herein.

FIELD

The present invention relates to the fields of dialysis apparatuses and electronic controllers and relates in particular to a method and a remote control unit and an application apparatus with such a remote control unit for remote control and processing of messages for a dialysis apparatus from a remote application apparatus.

BACKGROUND

Known modern, medical apparatuses such as e.g. dialysis apparatuses comprise an input and output unit for inputting and outputting data, which can often be designed as a touch-sensitive screen for controlling the apparatus, such as e.g. the hemodialysis apparatus 5008 from Fresenius Medical Care. Capacitive sensor technology is usually used for the operating interfaces of the dialysis apparatuses. U.S. Pat. No. 9,189,597, which is incorporated herein by reference in its entirety, provides an example of a touch-screen with capacitive sensor technology in which an additional piezo element layer with piezo elements is used to detect tactile feedback.

The dialysis apparatuses, in particular the displays thereof for operating and controlling the apparatus, are generally operated in clinical practice by a plurality of persons or by one person who, however, operates a plurality of medical, and possibly contaminated, apparatuses or patients in sequence and between such operations is therefore constantly required to carry out time-consuming disinfection so that touching the screen does not lead to undesired contamination in which e.g. pathogenic germs or micro-organisms cause cross-contamination, i.e. direct or indirect transfer of potentially harmful substances.

In order to avoid such transfer of pathogenic organisms and contamination it is known to carry out routine disinfection before and/or after any operation of, or contact with, the user interface of the dialysis apparatus, in particular when the user (the doctor or nurse) is working at another application apparatus (e.g. at another dialysis apparatus) or is in direct contact with a patient. For this purpose, the user may have to first disinfect his hands and/or the user interface of the dialysis apparatus, Only after this can be operate the user interface of the dialysis apparatus. Since this procedure is extremely time-consuming and laborious, there is a risk that it is omitted in therapeutic practice, which increases the risk of cross-contamination.

U.S. Patent Publication No. 2013/0018355 A1, which is incorporated herein by reference in its entirety, provides an example of a system for remote control of dialysis apparatuses by a remote control apparatus which is located in a control room.

U.S. Patent Publication No. 2013/0133036 A1, which is incorporated herein by reference in its entirety, provides an example of a system for remote access to a dialysis apparatus in order e.g. to permit the doctor or treating person to have access to the dialysis apparatus which may be located remote from, e.g. in the private surroundings of, the patient, without the doctor having to go to the dialysis apparatus in the patient's house.

SUMMARY

In an exemplary embodiment, the invention provides a method for controlling a medical apparatus by processing messages on a remote application apparatus, wherein the messages relate to the operation of the medical apparatus, the method comprising: detecting an activation signal on the application apparatus; receiving a message of the medical apparatus on the application apparatus; checking a safety criterion with an evaluation of a visual contact signal; and providing, in response to a result of checking the safety criterion being positive, a processing procedure for remote processing of the message on the application apparatus as long as the safety criterion is met.

In another exemplary embodiment, the invention provides a remote control unit for a remote application apparatus for remote control of a medical apparatus on the remote application apparatus by processing messages which relate to the operation of the medical apparatus, wherein the remote control unit comprises: an input interface, configured to detect an activation signal and to receive a message of the medical apparatus; and an identification device, configured check a safety criterion, wherein checking the safety criterion comprises automatically evaluating a visual contact signal; wherein the remote control unit is configured for remote processing of the message in order to carry out a remote processing procedure in the event of a result of checking the safety criterion being positive.

In yet another exemplary embodiment, the invention provides a remote application apparatus comprising a processor and a non-transitory computer-readable medium having processor-executable instructions stored thereon, the processor-executable instructions, when executed, facilitating performance of the following: detecting an activation signal from a medical apparatus; receiving a message of the medical apparatus; checking a safety criterion, wherein checking the safety criterion comprises automatically evaluating a visual contact signal; and remotely processing the message in the event of a result of checking the safety criterion being positive.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

When acknowledging messages, such as e.g. alarm messages which are output on and for the medical apparatus, it should or must be ensured that the treating person, who is working at another application apparatus and wishes to cause acknowledgement of the message—so to speak—remotely, also has visual contact with the patient of the medical apparatus in order to avoid erroneous operation.

Exemplary embodiments of the present invention improve control of a medical apparatus and in particular processing of messages for the medical apparatus, in particular for a dialysis machine, from a remote application apparatus. In particular, safety should be increased and the risk of cross-contamination reduced during operation of dialysis machines. Furthermore, the operating process is rendered more flexible and at the same time more efficient within the framework of dialysis.

In an exemplary embodiment, a method is performed for an input and output unit, in particular for a touch-screen, of a medical apparatus in particular a dialysis apparatus. The method is characterized in that remote processing of a message is allowed only on those remote application apparatuses which meet a safety criterion.

According to one aspect, a method for remote control of a medical apparatus on a remote application apparatus by the processing of messages which relate to the operation of the medical apparatus includes:
  detecting an activation signal on the application apparatus;
  receiving the respective message of the medical apparatus on the application apparatus;
  checking a safety criterion, wherein at least one visual contact signal is evaluated, and in the event of a positive result from the check:
    providing a remote operating procedure for remote control of the medical apparatus by remote processing of the respective message on the application apparatus as long as the safety criterion is met.

Within this application, the term 'remote control' is to be understood as relating to the processing of messages by or for a medical apparatus on a remote application apparatus. The remote processing can include the input and detection of an acknowledgement signal (processing signal). The processing signal is input in a conventional manner on a user interface of the application apparatus. However, alternatively, it may also be a case of a text input, a movement gesture or a voice signal. The remote processing of the messages includes inputting processing signals by the user on the application apparatus. The processing signals can be an acknowledgement of a message or one or more processing command(s) which are to be carried out on the medical apparatus. It is also possible for the processing signal not to be a binary signal for confirmation purposes but to include the inputting of values. The remote processing can therefore include detection of at least one processing signal and the transmission of the detected processing signal to the medical apparatus.

Exemplary embodiments of the invention provide an option for remote control of the medical apparatus. For this purpose, a remote processing procedure (hereinunder also shortened to processing procedure) should or must be implemented and initialized on the respective application apparatus. This allows for safe remote processing of messages for the dialysis apparatus to be carried out from the application apparatus. However, in other exemplary embodiments, direct processing of the message may take place on the dialysis apparatus transmitting the message. In other further exemplary embodiments, the remote processing option may be used and indirect processing of the message may take place on a remote apparatus, namely on the application apparatus.

A distinction is made between the provision of the processing procedure on the application apparatus (i.e. the installation thereof on the computer system of the application apparatus) and implementation (running of the application) thereof. After the provision of the processing procedure, implementation does not necessarily have to be carried out as described above. Implementation may take place in any case only after the safety criterion has been checked.

The processing procedure includes a signal exchange between the application apparatus and the medical apparatus to be remotely operated. This signal exchange can include digital and/or analog signals. The processing procedure provides in particular a user interface or sections thereof on the application apparatus, which comprise corresponding control fields and can be operated in accordance with the invention on the application apparatus in place of the control fields on the medical apparatus. It is also possible to form the entire user interface of the medical apparatus on the application apparatus, or only control fields which are currently to be operated. Therefore, it becomes possible to acknowledge messages, which are generated on the medical apparatus, on the application apparatus via the operation of a corresponding control field.

In accordance with exemplary embodiments of the invention, operating safety can be increased in that misuse by unchecked operation or intrusion by another apparatus can be reliably avoided. For this purpose, an additional component may be provided, i.e., an identification device, which is intended to check a safety criterion. It can be designed in particular to automatically check whether there is visual contact between the operating person at the application apparatus and the patient at the medical apparatus or with the medical apparatus per se.

Exemplary embodiments of the invention will be described hereinunder for a dialysis apparatus as an example of a medical apparatus, e.g. a hemodialysis apparatus or a peritoneal dialysis apparatus. However, a person skilled in the art will appreciate that the principles discussed herein can likewise be applied or transferred to other medical computerized apparatuses or (fluid-management) machines or blood-treatment apparatuses which are controlled via a touch-screen.

The medical apparatus can assume different roles: namely as an apparatus to be operated remotely or as an application apparatus. An apparatus is designated an application apparatus when a user is located directly in front of the application apparatus and e.g. is treating a patient or carrying out other activities at that location. The application apparatus does not necessarily have to be a medical apparatus; it can also be a central server, a mobile communications apparatus or a management or image processing computer.

In a preferred embodiment of the invention, the display is a capacitive touch-screen with multi-sensor functionality, which can also simultaneously detect touch. An example of such a touch-screen is described in more detail in U.S. Pat. No. 9,189,597, which is incorporated herein by reference in its entirety. The display constitutes a user interface (also called a monitor) and serves to detect the input signals (e.g. on input fields) for control and operation of the application apparatus. The display comprises interaction surfaces, switching elements, control fields etc. for control of the application apparatus. However, in accordance with exemplary embodiments of the invention, the display additionally comprises a remote processing region which is reserved for remote processing of a remote dialysis apparatus. This can be implemented e.g. by the superimposition of an additional window.

The activation signal serves to initiate the remote processing of messages. The activation signal is preferably transmitted only to selected application apparatuses, namely to target application apparatuses which have been configured in a definition phase. In so doing, it is possible to configure which target application apparatuses are fundamentally considered for a specific medical apparatus. In so doing, an admissibility condition can be evaluated which e.g. checks whether the medical apparatus to be remotely operated and the application apparatus are in the same room. Optionally, further conditions can also be defined. This is preferably carried out in a menu-controlled manner in the definition phase. However, the user also has the option of making a selection or of defining certain conditions and/or target application apparatuses. Depending on the embodiment of the invention, after detection of an activation signal on an application apparatus which fulfills the admissibility condition, and in the event of positive checking of the safety criterion, either a message or a sequence of messages can be handled remotely. This can also be specified in the activation signal (e.g. via the setting of a hit for the validity of the remote operation option).

The message is a status message with respect to the medical apparatus, such messages being classified in different safety levels. The different safety levels can likewise be configured in the definition phase. The messages may require at least the input of a confirmation or processing signal for acknowledgement of the message by a user. The messages can be output in different formats (e.g. visually and/or acoustically etc.). The message can be formed e.g. as an alarm. The messages can be present in a different mode. They can relate to different aspects of safety of the apparatus operation and can have a different risk potential. Depending on the mode of the message, different processing of the message may be appropriate or required. Thus, an alarm message which refers to a risk to the health of the patient can require immediate, high-priority processing in comparison to a status message relating to the battery status of a replacement module.

The processing signal can include an input on a touch-sensitive display, a text input, a selection from a menu or an acoustic or visual input, e.g. in the form of a gesture. The remote operation or remote processing therefore comprises the inputting of a processing or confirmation signal, e.g. for an alarm message, the input of a user signal (key press) on an operating field of the display on the remote application apparatus. The processing signal is biuniquely allocated to a message. The processing signal is detected, in accordance with exemplary embodiments of the invention, on an apparatus other than the apparatus on which the message was generated.

The safety criterion serves to check whether the respective application apparatus is authorized for remote processing of the respective message under consideration of the respective safety level of the message for the respective medical apparatus. Checking includes in particular whether visual contact exists between the user of the application apparatus and the medical apparatus to be remotely operated or the patient being treated with said apparatus. For this purpose, a visual contact signal is evaluated.

The visual contact signal represents a status of the user of the application apparatus and the respective medical apparatus (or the patient being treated therewith). In particular, with the visual contact signal, there is automatic detection of whether a visual contact exists between the user of the application apparatus and the medical apparatus and/or the patient attached to the medical apparatus. According to a first embodiment of the invention, it is specified via the visual contact signal whether a visual contact can exist in principle and, in accordance with a second embodiment of the invention, whether visual contact currently exists. In a preferred embodiment of the invention, a visual contact signal is requested for each message and is then allocated to the respective message. As already mentioned, in another embodiment of the invention, a plurality of messages (e.g. a sequence of messages) can also be processed by the visual contact signal of the first message.

According to one advantageous embodiment of the invention, the safety criterion is configured in a definition phase which chronologically precedes the actual remote control phase. Therefore, preconfiguration is possible in that the user is offered presets for the configuration of the safety criterion on a user interface, which presets the user merely needs to confirm in the simplest case. In this case a plurality of parameters can also be combined (e.g. corresponding room, maximum distance between the apparatuses, camera provided at the application apparatus, etc.).

According to a further advantageous embodiment of the invention, the safety criterion is defined specifically for each medical apparatus. Therefore, an extremely high level of flexibility can advantageously be achieved. A technical advantage is that medical complications and certain application scenarios can be covered in an extremely simple and uncomplicated manner (e.g. for an emergency dialysis patient who requires particularly intensive care, and therefore the remote operation options are to be extremely limited).

According to a further advantageous embodiment, the visual contact signal is evaluated by evaluation of a radio-frequency identification (RFID) chip, a near-field communication (NFC) module, a camera, by radio triangulation or by the evaluation of digital site plans. The digital site plans are room-apparatus allocations in a digital format which can be read and processed by software. With the aid of these site plans it is possible to automatically detect which application and medical apparatus is located in which room or which further apparatuses are likewise located in this room. This information can be used e.g. to select the target application apparatuses from the group of application apparatuses.

In a further advantageous embodiment, a selection of target application apparatuses is configured namely in a definition phase for each medical apparatus, remote operation or remote processing being possible on said target application apparatuses when the safety criterion is met. Thus the role can change between the application apparatus and the medical apparatus.

In a further advantageous embodiment, provision is made that during remote processing of messages on the application apparatus, a remote processing status is output by output of a remote processing signal in order to signal the remote processing to the outside (e.g. graphically or by the popping-up of a window with the title "Remote processing for medical apparatus xyz" or by some other separation of the user interface from the application apparatus per se and the portion of the user interface which is reserved for the remote processing of the medical apparatus).

In a further advantageous embodiment of the invention, the checking of the safety criterion takes place, in that a safety level of the associated message is evaluated in relation to the visual contact signal. Therefore, the checking of the safety criterion may always additionally include a further processing step, namely the evaluation of the respective message and/or of a status of the message (e.g. lower, middle or high safety risk of the message). A different status of a message may require the application of different safety criteria. In the embodiment of the invention described above, the method comprises the following step:

evaluating (determining) a safety level of the message. In that case, predefined categories of messages can be considered. This step is preferably carried out after receipt of the respective message.

According to a further aspect, the invention relates to a remote control unit for a medical application apparatus for remote control of a medical apparatus on the remote application apparatus by the processing of messages which relate to the operation of the medical apparatus, comprising:

an input interface which is intended to detect an activation signal and furthermore is intended to receive the respective message of the medical apparatus and comprising an identification device which is intended to check a safety criterion and in so doing to automatically evaluate a visual contact signal, and wherein the remote control unit is intended for remote processing of the respective message in the event of a positive checking result, provided that the safety criterion is met.

The identification device can be, inter alia, an optical sensor arrangement, e.g. a camera. It can also be an identification module for outputting signals on a graphic user interface of the application apparatus. The identification module can be software-based and monitor the data exchange between the application apparatus and the medical apparatus which is to be remotely controlled, according to a predefined protocol. Thus, e.g. a request signal (e.g. for carrying out a specific input) can be generated on the medical apparatus, which should or must then be answered in response thereto in a corresponding manner on the application apparatus. At that location, a check is then made by the identification module as to whether precisely the expected input has been effected, and therefore it is then assumed that visual contact exists between the apparatuses. Alternatively, additional request commands and responses can be requested. Alternatively or cumulatively, an RFID module or an NFC module can be designed to detect the presence of a person by RFID or NFC communication. An RFID/NFC receiver is designed for this purpose in or at the application apparatus and interacts with an RFID/NFC transmitter carried by the person. Otherwise, the identification device can comprise an acoustic sensor arrangement. Thus, commands for inputting an acoustical signal can be generated on the medical apparatus and output (directly to the medical apparatus), which commands are then answered by corresponding inputs on the application apparatus. Alternatively, the presence can be detected by radio triangulation or by a camera system.

In one advantageous embodiment of the invention, the identification device is arranged to define the safety criterion in a definition phase chronologically preceding the remote control phase.

In a further embodiment of the invention, provision is made that the identification device for evaluation of the visual contact signal evaluates an RFID chip, an NFC module, a camera and/or digital site plans and/or comprises a processor component which is intended to carry out radio triangulation.

In a further advantageous embodiment of the invention, within the scope of the checking of the safety criterion, the identification device is designed to evaluate a safety level of the respectively allocated message with respect to the visual contact signal. The advantage thus arises that the remote control procedure can be geared more flexibly to the respective safety level and can be adapted thereto.

In a further advantageous embodiment of the invention, the remote control unit comprises a remote control signal unit which is designed to indicate a remote processing status by outputting a remote processing signal to the application apparatus during implementation of the processing procedure (for remote control on the application apparatus). This has the advantage that the remote processing or remote control of the medical apparatus is activated directly on the respective application apparatus and in order thereby to represent the remote control status and to make it transparent to the outside in order to avoid erroneous intervention.

In a further advantageous embodiment of the invention, the remote control unit comprises a checking unit which is designed to determine for which medical apparatuses the respective application apparatus, to which the remote control unit is allocated, is admissibly activatable. The checking unit can be designed as a microprocessor component and as a component of the identification device. The checking unit can be in data exchange with a (e.g. central) database in which the admissible allocations between the respective medical apparatus to be remotely controlled and the application apparatus are stored. This has the technical effect that the admissible allocations can be centrally administered and uniformly applied for all apparatuses.

The checking unit can on the one hand—in the definition phase—serve to define admissible allocations of the medical apparatus and the application apparatus/remote control apparatus. The checking unit can on the other hand—in a control phase—be used to check whether the respective application apparatus can also be used for remote control of the medical apparatus.

According to a further aspect, the invention relates to a medical application apparatus with a remote control unit as described above. Thus the application apparatus can also be designed as a mobile terminal.

Exemplary embodiments of the invention provide a secured remote processing functionality of messages of the medical apparatus to be remotely operated on a remote application apparatus, such that the risk of contamination or cross-contamination can be reduced. Furthermore, calmness in a dialysis center with a plurality of treatment points can be retained even when only a few staff members are available in that acoustic alarm signals can be avoided since the respective message can also be handled from another apparatus. The reaction time can also be shortened since an otherwise necessary disinfection process when changing apparatuses can be avoided.

In the following detailed description of the figures, exemplary embodiments, which are not to be understood to be limiting, together with the features and further advantages thereof, will be discussed with the aid of the drawings.

Figure 1:
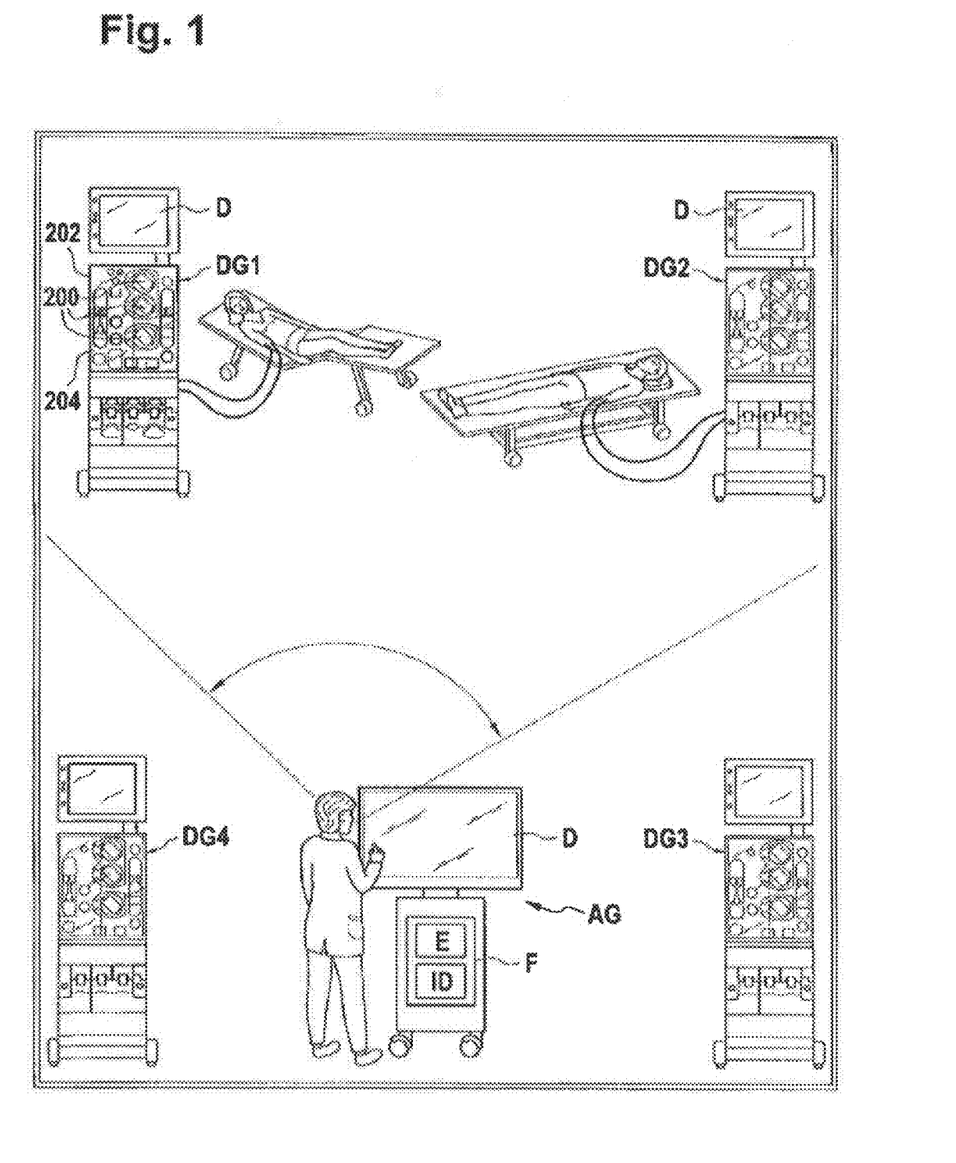
FIG. 1 depicts a schematic drawing of a dialysis station with a plurality of dialysis apparatuses and an application apparatus.

FIG. 1 depicts a schematic illustration of an exemplary dialysis station with a plurality of medical apparatuses, including dialysis apparatuses DG1, DG2, DG3, DG4 and patient beds with patients. Further apparatuses can also be operated in the dialysis station, at which users work and which are designated hereinunder as application apparatuses, including the depicted application apparatus AG. A dialysis apparatus can also have the role of an application apparatus if a user is working thereon and operates it. An application apparatus can likewise also have the role of a dialysis apparatus when e.g. the doctor is in the process of treating the patient at this dialysis apparatus and using the same for this purpose. An application apparatus therefore does not necessarily have to be a dialysis apparatus but can also e.g. be a central computer, a local electronic control apparatus or a mobile apparatus such as a laptop or a smartphone.

Dialysis apparatuses are known. In relation to this, reference is made to U.S. Patent Publication No. 2013/0018355 A1, which is incorporated herein by reference, and which provides examples of different blood treatment apparatuses, German Patent Application No. DE 197 426 33, which is incorporated herein by reference, provides an example for a dialysis apparatus which includes a touch-screen as an input and output interface.

The dialysis apparatuses DG1, DG2, DG3, DG4 may be operated and controlled via one or more displays D. Each display D serves as an input and output interface or as a user interface. A control unit is attached to each dialysis apparatus in a conventional manner via a suitable data connection. As schematically shown in FIG. 1, the dialysis apparatus DG1 includes an extracorporeal treatment module 202 as a central element. This can be secured against being inadvertently contacted by a transparent cover 204 which, in this case, is in the form of a two-leaf door. The extracorporeal treatment module 202 includes a multiplicity of operating components 200 in the form of different pumps (e.g. blood, substitute fluid), valves, syringes, holders, receptacles and the like. The operating components 200 can be located at different positions either within the dialysis apparatus DG1 or externally (at a connected component), i.e. also outside of the extracorporeal treatment module 202. Furthermore, the operating components 200 themselves can also be connected to the dialysis apparatus DG1 as an external, separate device via a corresponding connection and a data connection. In the exemplary embodiment illustrated in FIG. 1, a blood pump is shown in the upper central region of the extracorporeal treatment module 202. Located beneath it is a substitute fluid pump and, on the left-hand side below a heparin pump, a substitute fluid port. Further operating components 200 are located at the lower part of the extracorporeal treatment module 202. Furthermore, other measuring units, connections and/or other components can be formed in the extracorporeal treatment module 202.

The application apparatus AG includes a remote control unit F with an identification device ID and an input interface E. The remote control unit F provides for remote processing of messages and therefore for remote control of one or more dialysis apparatuses on the remote application apparatus AG. This relates in particular to the processing of messages which relate to the operation of one or more dialysis apparatuses which are to be operated remotely. The input interface F serves to detect an activation signal and to receive a respective message of a dialysis apparatus. The identification device ID is intended to check a safety criterion and in so doing to automatically evaluate a visual contact signal. In the event of this check of the safety criterion achieving a positive result, the remote control unit F is intended for a preconfigurable period of time for remote processing of the respective message as long as the safety criterion is met.

During dialysis operation, the status of a dialysis apparatus or of its operating components is detected for safety reasons. Corresponding status messages or messages of a general type are output for this purpose on the display of the dialysis apparatus. In this case, different safety levels are distinguished from messages. In one exemplary embodiment it is possible to distinguish between 3 classes of messages:
1. Alarm messages with high priority, which involve a safety risk and must be answered immediately.
2. Alarm messages with low priority,
3. Simple messages which do not necessarily need to be answered within a specific time phase.

The definition of the safety levels can be configured in accordance with exemplary embodiments of the invention such that in other examples more or fewer safety levels are detected and can be calculated in order to check a safety criterion. In the definition phase, e.g. various determinations can be made with respect to the safety levels: messages of class 1 require direct acknowledgement with a user present on site, i.e. at the actual dialysis apparatus sending the message (no option for remote processing of the message), while messages of class 2 permit indirect acknowledgement but only subject to a safety criterion which determines that the application apparatus must be in the same room. Messages of class 3 can also permit indirect acknowledgement without the application apparatus having to meet specific positional constraints.

The messages are output in a conventional manner at the respective dialysis apparatus on which they are detected, in particular on the display thereof. It is possible in accordance with exemplary embodiments of the invention to provide further flexibility for the doctor or the user. In accordance with exemplary embodiments of the invention, the message is output under specific circumstances (safety criterion at the target application apparatus being met) on an application apparatus on which the user is in the process of working. However, in order to satisfy safety requirements, the message is not output on just any application apparatus but only on dedicated apparatuses. For this purpose, e.g. in a definition phase a group of possible target application apparatuses can be determined in advance for each dialysis apparatus, these target application apparatuses being principally considered for remote handling of messages from and for the respective dialysis apparatus. In this case, the organization unit (e.g. the hospital) can specify rules and e.g. specify that fundamentally only those target application apparatuses are considered which are located in the same room as the respective dialysis apparatus, so that in principle visual contact can be established between a user working at an application apparatus and the respective dialysis apparatus.

In a preferred embodiment of the invention the safety criterion is determined to be that an identification device, in particular a person identification device, is provided at or on the application apparatus and is intended to identify whether a user is located in front of the application apparatus. The identification device can be e.g. an optical sensor or a camera. In another embodiment of the invention, it is possible via an identification module also to initiate and check a signal exchange between the application apparatus and the dialysis apparatus to be remotely operated, in order to ensure that the user in front of the application apparatus can also answer the commands or requests of the dialysis apparatus. Thus, e.g. a signal exchange can be implemented after the challenge-response process, in which the dialysis apparatus to be remotely operated transmits a request to the respective application apparatus and the user then causes this apparatus to answer via a response signal to the dialysis apparatus. A signal exchange between different apparatus components can likewise be started in that the request by the dialysis apparatus is e.g. a request for a gesture or movement which can be detected by the camera of the application apparatus. When a correct response is given, the safety criterion is deemed to be met, and therefore remote operation can be carried out on the application apparatus.

In order also to represent the aspect of the safety criterion of the field of vision in FIG. 1, a cone of vision is indicated starting from the application apparatus AG, this cone including, in this example, the dialysis apparatuses DG1 and DG2, while dialysis apparatuses DG3 and DG4 are located outside the field of vision. According to the configuration in the definition phase, although the application apparatus AG is fundamentally considered as a target application apparatus for remote operation by the dialysis apparatus DG3, it is located outside the range of the field of vision and thus cannot meet the safety criterion. The dialysis apparatus DG4 is located e.g. in a withdrawn position, and therefore right from the start it is not considered as a target application apparatus.

In an exemplary embodiment, a method is divided into a definition phase, in which the fundamental definitions and settings are configured, and a control phase. The definitions can be made by the user. For example, it is possible to configure which rules are to apply to the determination of the target application apparatus for a respective dialysis apparatus. Furthermore, in the definition phase, the parameters are configured for the safety criterion. Different parameters can also be coupled to conditions (e.g. safety criterion=parameter 1 AND parameter 2 OR parameter 3 AND NOT parameter 4). For this purpose, a menu can be provided on the user interface, in which one or a plurality of option(s) can be selected, such as e.g. "Position of the application apparatus in the same room", "Camera provided on the application apparatus and usable", "Minimum distance between the apparatuses not over x meters" etc. In the chronologically later control phase, a specific dialysis apparatus is then remotely operated or remotely controlled in that all or selected commands or inputs are no longer detected on the display of the dialysis apparatus but on a specific application apparatus which meets the predefined safety criterion and for as long as it meets same.

In the definition phase it is also possible e.g. to configure that messages can also be selectively acknowledged or answered directly on the respective dialysis apparatus when the user is located e.g. purely by chance in front of the respective message-triggering dialysis apparatus at the time of the message and optionally, and therefore—so to speak—additionally, further remote operation on the application apparatus becomes possible. It is likewise possible to configure such that in the case of remote operation, only operation by the application apparatus is then accepted and not direct operation on the dialysis apparatus. Furthermore, a time interval can also be configured which determines in which time period specific messages must be answered and acknowledged.

In the definition phase it is also possible that a distinction is made between different safety levels. Thus, a high-priority message (e.g. alarm signal) is processed differently from a low-priority message. A high-priority message can e.g. additionally be coupled to the triggering of a visual (or alternative) alarm signal on the dialysis apparatus or on the application apparatus. This has the technical effect that in the event of a relevant alarm, the user is informed about a plurality of different signal types.

The remote operation generally includes the acknowledgement of messages which are output on the display. For this purpose, the application apparatus AG also comprises a display D on which the messages are output and on which the processing of the output message takes place, in particular via the inputting of an acknowledgement signal. However, the remote operation can also include a plurality of steps which require a sequence of inputs on the touch-screen.

Figure 2:
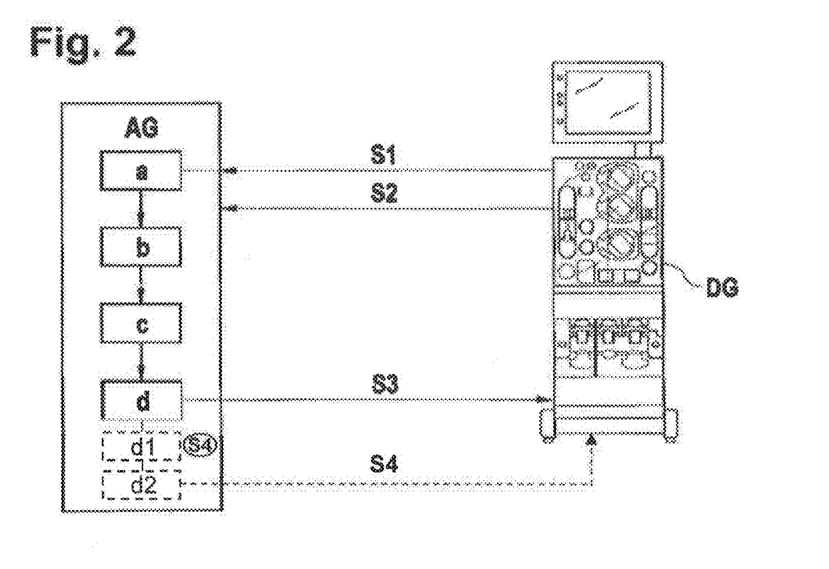
FIG. 2 schematically depicts the signal exchange between an application apparatus and a dialysis apparatus.

A method in accordance with an exemplary embodiment of the invention is explained in more detail hereinunder with reference to FIG. 2. After the definition phase is completed all configurations are determined. In the control phase, the dialysis apparatus DG should be remotely controlled via the (or on the) application apparatus AG because e.g. the doctor is working at this apparatus and, in the event of messages on the dialysis apparatus DG, does not want to bring about the risk of cross-contamination by bringing pathogens into contact with the "foreign" display of the dialysis apparatus DG without prior disinfection. This risk can be eliminated in that the doctor does not "leave" his field of action on the application apparatus AG but can nevertheless effect control of the dialysis apparatus DG. For this purpose, an activation signal S1 is first generated on the dialysis apparatus DG and transmitted to the application apparatus AG and received there in step a. This has the technical advantage that only actually intended remote operation is carried out and errors caused by undesired operations by other people can be avoided. Thus e.g. remote operation is impossible when no activation signal S1 has been sent. Safety can therefore be increased. Only after receipt of the activation signal S1 can remote operation be triggered. For this purpose, a specific message S2 is generated on the dialysis apparatus DG and sent to the application apparatus AG. In step b, the message can be received on the application apparatus AG and output on the display of the application apparatus AG. Preferably, a wireless message exchange is provided between the dialysis apparatus DG and application apparatus AG (e.g. mobile radio connection, Bluetooth etc.), or a wired message exchange (e.g. via a network connection) is provided.

Optionally, the message S2 can also be presented directly on the display of the dialysis apparatus DG. In step c, a (predefined) safety criterion for the message S2 and for the respective dialysis apparatus DG is checked. In particular, a check is made whether visual contact exists between the user working at the application apparatus AG and the dialysis apparatus DG to be operated remotely. In addition, the safety step of the respective message S2 can optionally be checked if e.g. it is determined in the definition phase that high-priority messages can be acknowledged only directly on the dialysis apparatus DG itself and are fundamentally not accessible for remote acknowledgement, while low-priority messages are accessible for remote acknowledgement. In more complex embodiments of the invention, still further conditions and linkages can be defined at this point. After the safety criterion has been checked for compliance, in step d the processing of the message S2 on the application apparatus AG is enabled, and a processing or acknowledgement signal S3 is sent from the application apparatus AG to the dialysis apparatus DG. Alternatively or additionally, two further steps d1 and d2 can be carried out which are illustrated in more detail in FIG. 2 with dashed lines. In step d1, an acknowledgement signal S4 is detected on the application apparatus AG, preferably on the touch-screen display. In step d2, the detected acknowledgement signal S4 is transmitted to the dialysis apparatus DG for control purposes and is processed accordingly at that location.

Figure 3:
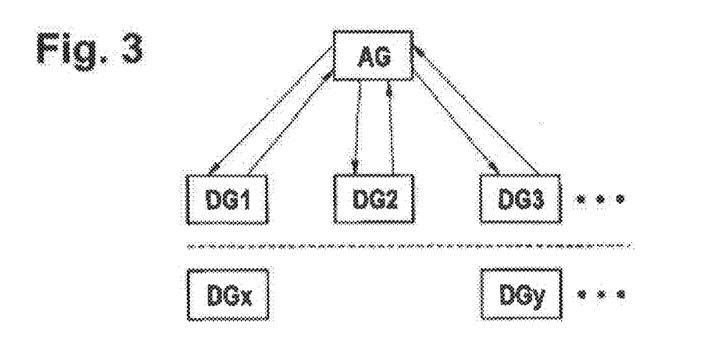
FIG. 3 depicts an exemplary embodiment in which an application apparatus controls a plurality of dialysis apparatuses.

FIG. 3 shows an exemplary embodiment in which a specific application apparatus AG can fundamentally control a plurality of different dialysis apparatuses DG1, DG2, DG3, ... DGx, DGy, .... However, as shown in FIG. 3 by the horizontally extending dashed line, the application apparatus AG meets the safety criterion (e.g. visual contact) only for some of the dialysis apparatuses DG1, DG2, DG3. The dialysis apparatuses DGx and DGy are located outside the field of vision and thus cannot be controlled from the application apparatus AG. In the definition phase, it is possible to configure whether the remote processing (remote acknowledgement) of messages can be effected by the dialysis apparatus meeting the safety criterion in the same time phase, so to speak in an interleaved mode or only sequentially. In the first case, it is ensured by additional measures that the respective remote control on the application apparatus AG is also allocated to the correct dialysis apparatus. This can preferably be implemented by an additional signal or data exchange according to a predefined protocol between the application apparatus AG and the dialysis apparatus.

Figure 4:
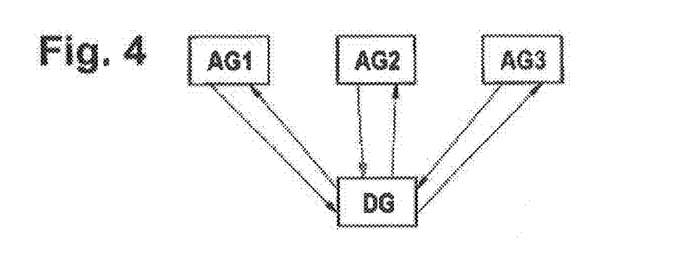
FIG. 4 depicts an exemplary embodiment in which a plurality of application apparatuses control a dialysis apparatus.

FIG. 4 shows an exemplary embodiment in which a dialysis apparatus DG can be remotely controlled by different application apparatuses AG1, AG2, AG3 when they meet the safety criterion. It is also possible in this case to configure that the remote control is possible so to speak in the parallel mode on the different apparatuses AG1, AG2, AG3 in order to provide the nurse or doctor with greater flexibility. He can then specify for operation the application apparatus AG which is the next most suitable or the most suitable for him. For this purpose, it should or must then be ensured that the activation signal S1 and the respective message S2 are transmitted to all application apparatuses AG1, AG2, AG3.

The two arrows pointing in alternate directions between the respective application apparatus(es) AG, AG1, AG2, AG3 and the dialysis apparatus(es) DG, DG1, DG2, DG3 in FIGS. 3 and 4 are each intended to represent the exchanged messages, in particular the activation signal S1 and the processing or acknowledgement signal S3.

In a preferred embodiment, the remote control functionality is determined. This can take place with respect to scope (which mode of messages can be accessible to remote processing) or with respect to a time phase (in which time period the remote processing is admissible).

In order to avoid cross-contamination and to increase ease of operation, in one embodiment of the invention an option is created for bringing the complete operating screen of a dialysis machine onto the screen of an application apparatus, wherein the application apparatus is located remote from the dialysis machine. Alternatively, only components of the screen which are relevant e.g. for the message S2 can be transferred to the application apparatus AG. In so doing, an automatic check can be made as to whether the application apparatus AG also has the necessary functionalities to present the operating screen and to detect corresponding inputs and whether it meets the safety criterion. Direct processing of messages S2 on the dialysis apparatus sending the message is therefore no longer absolutely necessary. During work with contact with a patient at an application apparatus AG, in accordance with exemplary embodiments of the invention, safe remote operation laid down by set rules at precisely this application apparatus AG is possible for a remote dialysis apparatus sending the message, without causing the risk of cross-contamination.

For this purpose, the apparatuses or machines or electronic apparatuses are networked with one another (e.g. via a local network or a wide area network (WAN) or via the Internet etc.). Each machine uses the identification device allocated thereto (e.g. by contactless techniques such as NFC or RFID) to recognize whether a user is so close that he can see and remotely operate the remote dialysis apparatus DG. At the same time, the authorization of the user located in proximity thereto is considered. In an identifier transmitted, e.g. by NFC, RFID or by reading of a SmartCard, the authorization level of the user is encoded or is called up from a database on the basis of the transmitted identifier. Thus, inputs of different groups of people are processed differently. An input by a doctor can e.g. be allocated a higher priority than that of a nurse or vice versa.

In the case of messages and alarms at dialysis apparatuses, a message with the position of the dialysis apparatus sending the message can be output only to those application apparatuses close to which a user has been detected (e.g. with the identification device ID). The positioning of the machine sending the message can take place e.g. via the evaluation of a room plan. The same method can be used in the case of other, stationary, application apparatuses. In the case of mobile application apparatuses, the current position of the user can be detected automatically by appropriate sensors. This can take place e.g. by locating using the sensing components located in the dialysis apparatuses or by radio triangulation.

Furthermore, for the outputting of messages and alarms for each message S2, the vicinity into which it may be transmitted for remote access is defined. It is thus possible e.g. to establish that a critical alarm such as e.g. a detected needle displacement of the venous access of a dialysis patient can be transmitted only to application apparatuses in the immediate proximity of the dialysis apparatus sending the message, while e.g. warnings for the non-achievement of the treatment target with respect to dialysis quality can also be transmitted over greater distances. Therefore, in an advantageous manner, for each operating/alarm situation a vicinity is defined which allows operation equivalent to the direct operation at the dialysis apparatus via remote access.

In order reliably to avoid the user carrying out remote accesses to machines which are not within his range of vision or field of view (and thus for which be could not judge the status of the patient), a vicinity is defined for each dialysis apparatus having the target application apparatuses admissible for remote access. In the simplest case, this is a treatment room. This definition can be stored in a central database and therefore be used uniformly for all apparatuses.

In one exemplary embodiment, the identification module of the remote control unit F is designed to display a room plan on the application apparatus AG. This can take place alternatively to the activation signal S1 and then indicates that a remote intervention is to be initiated for a remote dialysis apparatus. On the superimposed room plan, the user presses on the location of the relevant dialysis apparatus sending the message. The identification module then causes the dialysis apparatus to send e.g. a visual signal such as a traffic light picture (e.g. flashing sequence), an identification sign. The screen of the dialysis apparatus is then transferred to the screen of the application apparatus AG in front of which the user is standing.

Via the remote processing signal (e.g. in the form of a special frame around the user's screen) the user is informed that remote access is possible. The user can now operate the other dialysis apparatus from his current position at the application apparatus AG. After termination of the remote access, the "remotely processed" machine indicates that it is "free" again.

It is noted that the description of the invention and the exemplary embodiments are fundamentally to be understood to be non-limiting with respect to a specific physical implementation of the invention. All features explained and illustrated in conjunction with individual embodiments of the invention can be provided in different combinations in the subject matter in accordance with the invention in order to achieve the advantageous effects thereof at the same time.

The scope of protection of the present invention is set by the claims and is not limited by the features explained in the description or shown in the figures.

For a person skilled in the art, it will be appreciated that the invention can be used not just for dialysis apparatuses but also for other medical apparatuses which comprise a user interface for operation of the apparatus. Furthermore, the components of the remote control unit F can also be embodied in a distributed manner on a plurality of physical products.

It will be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein performed by computing devices and components thereof may be carried out according to stored instructions and/or installed applications.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A method for remotely controlling a medical apparatus using a remote control apparatus, the method comprising:
   detecting, by the remote control apparatus, an activation signal;
   receiving, by the remote control apparatus, a message of the medical apparatus;
   checking, by the remote control apparatus, a safety criterion, wherein checking the safety criterion comprises detecting whether visual contact exists between a user of the remote control apparatus and the medical apparatus based on evaluating a visual contact signal; and
   in response to detecting that visual contact exists between the user and the medical apparatus, enabling, by the remote control apparatus, remote processing of messages for the medical apparatus on the remote control apparatus.

2. The method according to claim 1, wherein the safety criterion is configured in a definition phase.

3. The method according to claim 1, wherein different safety criteria are defined for different medical apparatuses of a plurality of medical apparatuses.

4. The method according to claim 3, wherein a safety criterion defined for a first medical apparatus corresponding to an emergency patient is relatively more limited as to remote operation options relative to a safety criterion defined for a second medical apparatus corresponding to a non-emergency patient.

5. The method according to claim 1, wherein evaluating the visual contact signal comprises evaluating a radio-frequency identification (RFID) chip, evaluating a near-field communication (NFC) module, utilizing a camera, utilizing radio triangulation, and/or evaluating digital site plans.

6. The method according to claim 1, wherein checking the safety criterion further comprises evaluating a safety level of a message of the medical apparatus, wherein different safety levels correspond to different safety criteria.

7. The method according to claim 6, wherein messages of the medical apparatus include messages of at least two safety levels, including:
   alarm messages corresponding to a high priority; and
   alarm messages corresponding to a low priority.

8. The method according to claim 7, wherein remote processing is prohibited for alarm messages corresponding to a high priority; and
   wherein remote processing is allowed for alarm messages corresponding to a low priority.

9. The method according to claim 8, wherein messages of the medical apparatus further include simple messages corresponding to a third safety level, wherein remote processing is allowed for simple messages without having to meet positional constraints.

10. The method according to claim 1, further comprising:
    during a definition phase for each medical apparatus of a plurality of medical apparatuses, selecting one or more target remote control apparatuses.

11. The method according to claim 1, wherein while remote processing is being carried out, a remote processing signal is output by the remote control apparatus to indicate a remote processing status.

12. The method according to claim 1, wherein detecting whether visual contact exists between the user and the medical apparatus is further based on evaluation of a room plan.

13. The method according to claim 1, wherein the remote control apparatus is a mobile device of the user, and wherein detecting whether visual contact exists between the user and the medical apparatus is further based on detecting a current position of the user using sensors of the mobile device.

14. The method according to claim 1, further comprising:
    determining whether or not to transmit an alarm message to the remote control apparatus based on a distance between the remote control apparatus and the medical apparatus.

15. A remote control apparatus for remote control of a medical apparatus, wherein the remote control apparatus comprises a processor and a non-transitory computer-readable medium having processor-executable instructions stored thereon, wherein the processor-executable instructions, when executed by the processor, facilitate:

detecting an activation signal on the remote control apparatus;

receiving a message of the medical apparatus on the remote control apparatus;

checking a safety criterion, wherein checking the safety criterion comprises detecting whether visual contact exists between a user of the remote control apparatus and the medical apparatus based on evaluating a visual contact signal; and     in response to detecting that visual contact exists between the user and the medical apparatus, enabling remote processing of messages for the medical apparatus on the remote control apparatus.

16. The remote control apparatus according to claim 15, wherein the processor-executable instructions, when executed by the processor, further facilitate:

defining or reading the safety criterion in a definition phase.

17. The remote control apparatus according to claim 15, wherein evaluating the visual contact signal comprises:

evaluating a radio-frequency identification (RFID) chip, evaluating a near-field communication (NFC) module, utilizing a camera, utilizing radio triangulation, and/or evaluating digital site plans.

18. The remote control apparatus according to claim 15, wherein checking the safety criterion further comprises evaluating a safety level of a message of the medical apparatus, wherein different safety levels correspond to different safety criteria.

19. The remote control apparatus according to claim 15, wherein the processor-executable instructions, when executed by the processor, further facilitate:

while remote processing is being carried out, indicating a remote processing status by outputting a remote processing signal.

20. The remote control apparatus according to claim 15, wherein the processor-executable instructions, when executed by the processor, further facilitate:

determining for which medical apparatuses the remote control apparatus is usable for remote processing.

21. A non-transitory computer-readable medium having processor-executable instructions stored thereon for remote control of a medical apparatus using a remote control apparatus, wherein the processor-executable instructions, when executed, facilitate:

detecting an activation signal on the remote control apparatus;

receiving a message of the medical apparatus on the remote control apparatus;

checking a safety criterion, wherein checking the safety criterion comprises detecting whether visual contact exists between a user of the remote control apparatus and the medical apparatus based on evaluating a visual contact signal; and     in response to detecting that visual contact exists between the user and the medical apparatus, enabling remote processing of messages for the medical apparatus on the remote control apparatus.

22. The non-transitory computer-readable medium according to claim 21, wherein the processor-executable instructions, when executed, further facilitate:

while remote processing is being carried out, indicating a remote processing status by outputting a remote processing signal.

23. The non-transitory computer-readable medium according to claim 21, wherein the processor-executable instructions, when executed, further facilitate:

determining for which medical apparatuses the remote control apparatus is usable for remote processing.

\* \* \* \* \*